(12) United States Patent
Wang et al.

(10) Patent No.: US 10,846,868 B1
(45) Date of Patent: Nov. 24, 2020

(54) METHODS FOR ALIGNING IMAGES OF DIGITAL PCR CHIPS

(71) Applicants: Yan Wang, San Diego, CA (US); Cory McCluskey, San Diego, CA (US)

(72) Inventors: Yan Wang, San Diego, CA (US); Cory McCluskey, San Diego, CA (US)

(*) Notice: Subject to any disclaimer, the term of this patent is extended or adjusted under 35 U.S.C. 154(b) by 0 days.

(21) Appl. No.: 16/889,574

(22) Filed: Jun. 1, 2020

(51) Int. Cl.
*G06T 7/33* (2017.01)
*C12Q 1/686* (2018.01)

(52) U.S. Cl.
CPC ............... G06T 7/33 (2017.01); C12Q 1/686 (2013.01); *G06T 2207/30204* (2013.01)

(58) Field of Classification Search
CPC ................................. G06T 7/33; C12Q 1/686
USPC ........................................................ 702/19
See application file for complete search history.

*Primary Examiner* — Jerry Lin
(74) *Attorney, Agent, or Firm* — Lili Chen

(57) ABSTRACT

Disclosed is a method for aligning images of high-density signals of a dPCR chip with high precision and accuracy, which assigns each signal spot on an dPCR image to a unified grid. More specifically, the invention provides methods for adjusting the coordinates of signal spots in an image, and aligning the adjusted image to the unified grid by aligning to features of a fiducial marker built in the chip.

9 Claims, 6 Drawing Sheets

METHODS FOR ALIGNING IMAGES OF DIGITAL PCR CHIPS

FIELD OF THE INVENTION

This invention relates to methods for image processing and analysis, especially relates to methods for making alignment of images with high-density spots on a dPCR microchip.

BACKGROUND OF THE INVENTION

Polymerase chain reaction (PCR) is a method that uses DNA polymerization reaction to generate millions and billions of nucleic acids of interest, called target sequences. It performs repeated cycles of denaturing of double-stranded DNA, annealing of primers to target sequences, and extending of primers to generate copies of target sequences. PCR is an indispensable technique in molecular biology that is widely used to detect, identify, obtain and quantitate a DNA/RNA sequence of interest.

Digital PCR (dPCR) is a refinement of PCR technologies that allows absolute quantification of nucleic acid strands and sensitive detection of rare DNA targets. The dPCR improves upon conventional PCR by separating one PCR sample into a large number of partitions to perform a large number of PCRs in parallel. The PCR sample is partitioned such that each partition on average contains no more than one target nucleic acid molecule, that is, each partition approximately contains either 1 or 0 target nucleic acid molecule. By detecting partitions with positive amplifications, digital PCR enables absolute quantification of target nucleic acids in a sample. The two major types of digital PCRs are droplet-based dPCR where a PCR sample is partitioned into a large number of oil-water droplets, and chip-based dPCR where a PCR sample is partitioned into a large number of micro-wells in a dPCR chip. A typical dPCR chip has a size of about 1 cm×1 cm and can contain 20,000 or more micro-wells. The amplification products generated in the micro-wells are conveniently detected by emissions from fluorescent probes used to label the PCR products. The analysis of dPCR results involves processing and analyzing the images of the fluorescent emissions in micro-wells of dPCR chips.

Real time digital PCR is a digital PCR that monitors the PCR progression in each micro-well during PCR amplification cycles. A picture of fluorescent emissions of micro-wells in a dPCR chip is taken at a preset interval during the process of dPCR. Multiple images of the dPCR chip need to be analyzed at the end of real time dPCR. The imaged is first processed to obtain peak intensity and position coordinate for wells on the dPCR chip. In order to analyze data on the dPCR chip, fluorescent signals from wells on the dPCR chip need to be aligned in different images of the same chip. There are challenges in alignment of such high-density array of signals. Since the density of micro-wells in the dPCR chip is very high, small misalignment can lead to wrong assignment of a large number of micro-wells. Micro-wells at edges of dPCR chips have high error rates or high number of no signal wells and cannot be used as the base for alignment. Xia et al. (US patent publication No. 20080253633A1) uses a series of peak intensities at the edge of an array for image alignment. Because signals at edges of dPCR chips are not reliable, this method cannot be applied in the alignment of multiple images in dPCR assays. In another method (US patent publication No. 20040006431A1) disclosed by Bartell et al., it uses one or more control features to align signal spots in microarrays. Microarrays has much lower density of signal spots than that of the dPCR chips. The method used in microarray analysis may not provide sufficient resolution in the alignment of dPCR images where small misalignment can result in dislocation of a large number of micro-wells.

SUMMARY OF THE INVENTION

In view of the difficulties and problems outlined above, it is one objective of the invention to provide a method for aligning multiple images of high-density signals of a dPCR chip with high precision and accuracy, which assigns each signal spot on an image to a unified grid that comparison of different images can be based on. More specifically, the invention provides methods for adjusting the coordinates of signal spots in an image so that the adjusted image can be aligned with a unified grid, and then aligning the adjusted image to the unified grid by aligning features of a fiducial marker built in the chip.

In one embodiment of the invention, there provides a method for aligning an image of signals of micro-wells of a dPCR chip to a grid, comprising the steps of: 1) obtaining position coordinate (x,y) for each signal of micro-wells of the dPCR chip; 2) adjusting y-coordinates of signals of micro-wells of the dPCR chip using a y-coordinate break point method to obtain adjusted y'-coordinates for signals and identify rows of signals of micro-wells in the dPCR chip; 3) adjusting x-coordinates of signals of micro-wells of the dPCR chip using a x-coordinate break point method to obtain adjusted x'-coordinates for signals of micro-wells of the dPCR chip; and 4) aligning adjusted coordinates (x', y') of signals of micro-wells of the dPCR chip to a grid by aligning features of a fiducial marker built in the dPCR chip.

In some embodiments of the invention, the y-coordinate break point method comprises the steps of: a) sorting y-coordinates of all the signals of micro-wells of the dPCR chip in an ascending order; b) keeping adjusted y'=y, if it is possible to use break points in sorted y'-coordinates to separate one row of signals from an adjacent row of signals; c) if it is not possible to directly use break points to separate one row of signals from an adjacent row of signals, adjusting y-coordinate of each signal as following: y'=y+k*x, wherein y' is adjusted y-coordinate, y is raw y-coordinate, x is raw x-coordinate, and k is a correction factor that can be changed; d) sorting y'-coordinates of all the signals in an ascending order and finding an appropriate $k_c$ such that it is possible to use break points in sorted y'-coordinates to separate one row of signals from an adjacent row of signals; and e) obtaining adjusted y'-coordinates for signals of micro-wells in the dPCR chip, wherein y'=y+$k_c$*x.

In some embodiments of the invention, the x-coordinate break point method comprises the steps of: a) sorting x-coordinates of signals of selected rows of micro-wells of the dPCR chip in an ascending order; b) keeping adjusted x'=x, if it is possible to use break points in sorted x'-coordinates to separate one column of signals from an adjacent column of signals; c) if it is not possible to directly use break points to separate one column of signals from an adjacent column of signals, adjusting x-coordinate of each signal as following: x'=x+k*y, wherein x' is adjusted x-coordinate, y is raw y-coordinate, x is raw x-coordinate, and k is a correction factor that can be changed; d) sorting x'-coordinates of signals in an ascending order and finding an appropriate $k_c$ such that it is possible to use break points in sorted x'-coordinates to separate one column of signals from an adjacent column of signals; and e) obtaining adjusted x'-coordinates for signals of micro-wells in the dPCR chip, wherein x'=x+$k_c$*y.

In some embodiments of the invention, the selected rows of signals comprise all the identified rows of signals.

In some embodiments of the invention, the selected rows of signals are odd number or even number rows of signals, wherein the x-coordinate break point method is used separately on signals of odd number or even number rows to obtain adjusted x'-coordinates for all the signals of micro-wells in the dPCR chip.

In one embodiment of the invention, there provides a method for aligning an image of signal spots of micro-wells of a dPCR chip to a grid, comprising the steps of: 1) obtaining position coordinate (x,y) for each signal spot of micro-wells of the dPCR chip; 2) selecting a number of random signal spots and calculating root mean square distance between each selected signal spot and its nearest grid spot; 3) adjusting coordinates of the selected signal spots to find a best fit adjustment that the average root mean square distance for the selected random signal spots is at a minimum value; 4) performing the best fit adjustment to all the signal spots to obtain adjusted coordinates for all the signal spots; and 5) aligning adjusted coordinates of signal spots of micro-wells of the dPCR chip to the grid by aligning to a fiducial marker in the dPCR chip. In some embodiments, the number of selected random signal spots is at least 10, 20, 30, 40, 50, 60, 70, 80, 90, 100, 200, 500 or 1000.

In some embodiments, the coordinates of the selected signal spots are adjusted as following: x'=x+k*y, y'=y−k*x, wherein x' is adjusted x-coordinate, y is adjusted y-coordinate, x is raw x-coordinate, y is raw y-coordinate, and k is a correction factor that can be varied.

In some embodiments, the coordinates of the selected signal spots are adjusted as following: x'=x+a, y'=y+b, wherein x' is adjusted x-coordinate, y is adjusted y-coordinate, x is raw x-coordinate, y is raw y-coordinate, a is a correction factor that can be varied, and b is a correction factor that can be varied.

DETAILED DESCRIPTION

Definitions

Figure 1:
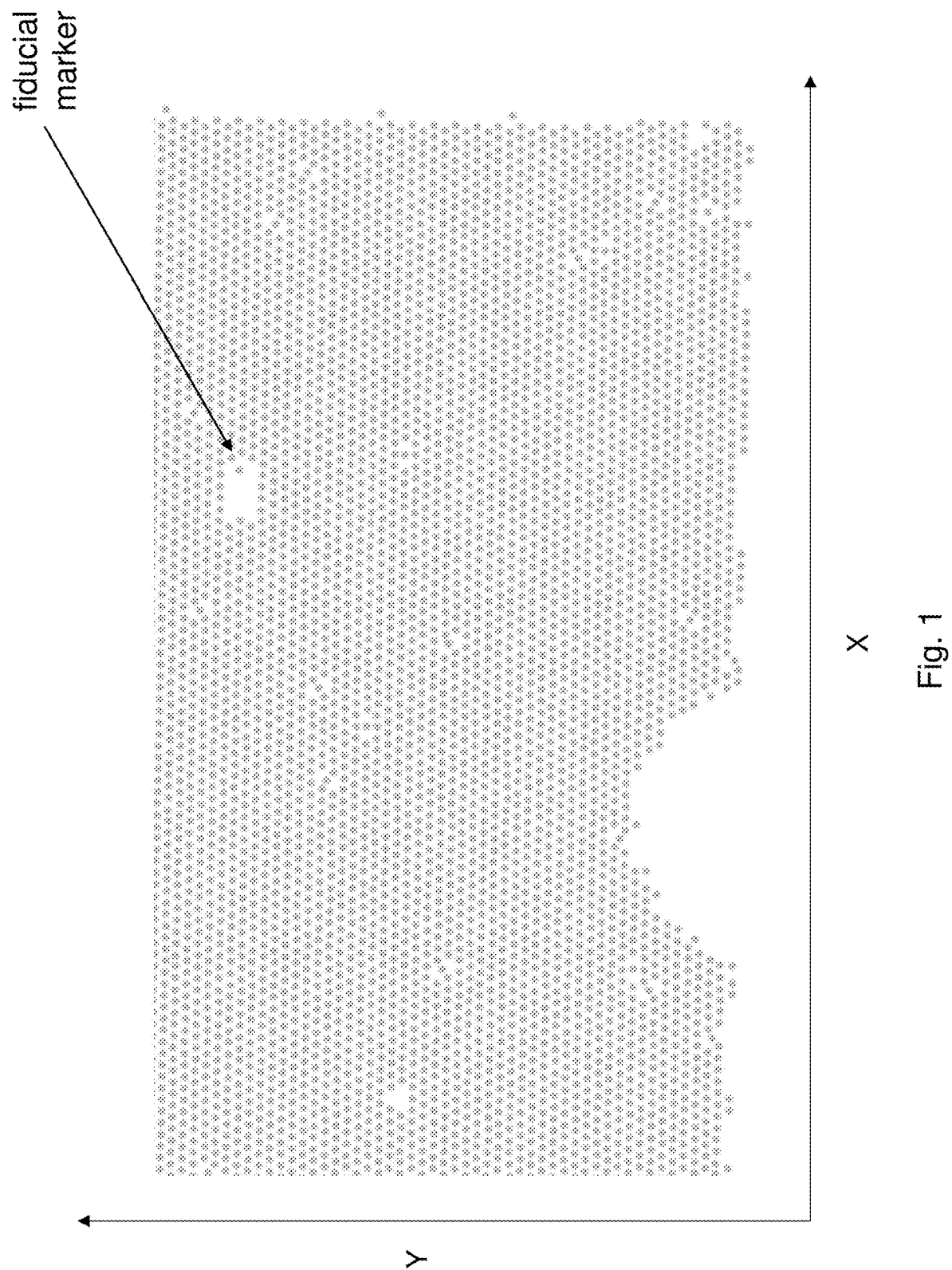
FIG. 1 is an image of fluorescence signals of micro-wells on a dPCR chip.

Unless otherwise defined, all technical and scientific terms used herein have the same meaning as commonly understood by one of the ordinary skills in the art to which this invention belongs.

The term "a" and "an" and "the" as used to describe the invention, should be construed to cover both the singular and the plural, unless explicitly indicated otherwise, or clearly contradicted by context. Similarly, plural terms as used to describe the invention, for example, nucleic acids, nucleotides and DNAs, should also be construed to cover both the plural and the singular, unless indicated otherwise, or clearly contradicted by context.

Real-time digital PCR is a digital PCR that monitors the generation of PCR products in a large number of micro-wells in a dPCR chip while PCR amplification is in progression. It employs the amplification characteristics of each well to determine false or true positive amplifications. Pictures of fluorescent emissions of micro-wells in a dPCR chip are taken at preset intervals during the process of dPCR. Pictures can be taken for every one or several PCR cycles. For example, pictures of a dPCR chip can be taken at every five PCR cycles and 8 pictures will be obtained for a 40-cycle dPCR. Each of thousands of wells in the dPCR chip need to be aligned between these eight different dPCR images for analyzing the real-time dPCR result.

In one embodiment of the invention, there provides A method for aligning an image of signals of micro-wells of a dPCR chip to a grid, comprising the steps of: 1) obtaining position coordinate (x,y) for each signal of micro-wells of the dPCR chip; 2) adjusting y-coordinates of signals of micro-wells of the dPCR chip using a y-coordinate break point method to obtain adjusted y'-coordinates for signals and identify rows of signals of micro-wells in the dPCR chip; 3) adjusting x-coordinates of signals of micro-wells of the dPCR chip using a x-coordinate break point method to obtain adjusted x'-coordinates for signals of micro-wells of the dPCR chip; and 4) aligning adjusted coordinates (x', y') of signals of micro-wells of the dPCR chip to a grid by aligning to features of a fiducial marker built in the dPCR chip.

Real time dPCR assays uses an inert and passive fluorescent dye to indicate which micro-wells in a dPCR chip contain PCR reagents. The fluorescence signal of the passive fluorescent dye is not influenced by the PCR and is present in all the micro-wells having the passive fluorescent dye independent of the occurrence of a PCR process. The signals from a passive fluorescent dye, for example, carboxyrhodamine (ROX), can be used to identify micro-wells with PCR reagents and locate rows and columns for micro-wells on a dPCR chip.

A dPCR chip typically has 20,000 micro-wells at a dimension of 1 cm×1 cm. An ideal dPCR image is a high-density array with 20,000 signal spots. In real practice, some micro-wells may not receive PCR reagents and give out no fluorescent signals. The micro-wells on edges of a dPCR chip have most variations due to uneven partitions and optical issues. Dusts, bubbles or other artifacts can also lead to imperfections in dPCR images. The accurate alignment of micro-wells across different dPCR images is critical because a minor misalignment can disrupt the matching relationship of the reaction wells and lead to complete corruption of the analysis.

FIG. 1 shows an exemplary image of ROX fluorescence signals of micro-wells on a dPCR chip. The micro-wells on the dPCR chip are arranged in regular horizontal rows and vertical columns. It can be seen from the image that signals from micro-wells close to the edge of the dPCR chip show highest variability. The rows and columns close to the edge of the dPCR cannot be used reliable reference points for alignment. As shown in FIG. 1, a fiducial marker is located at a known position inside the dPCR chip which can be used as a reference point for adjusting coordinates of signals of micro-wells to align the image to a unified grid that is shared cross different images. It also can be seen that the image is tilted in regard to the X-Y coordinate plain.

A dPCR image of fluorescent emissions is digitalized pixel-by-pixel to obtain peak intensity and position coordinate (x,y) for each micro-well on the dPCR chip. After image processing, a set of (x, y) coordinates representing positions of micro-wells in a dPCR chip are obtained for each image. The (x, y) coordinate originally obtained for each micro-well on the fluorescence image is called the raw coordinates to be differentiated from the coordinates that are adjusted later. The coordinates of the same micro-well in a dPCR chip are different among multiple images of the same dPCR chip due to slight changes in camera shooting angles and/or data processing variations. In some embodiment of the invention, a method is provided to align positions of micro-wells among different images by converting the raw (x, y) coordinate of each micro-well into a grid coordinate that defines the row number and column number of each micro-well in a unified grid for the dPCR chip. Micro-wells with the same grid coordinate across different images can be easily identified as the same micro-well on a dPCR chip.

In some embodiment of the invention, it provides a y-coordinate break point method for separating rows of signals in an image by finding a break point in y-coordinates of signals sorted in an ascending order. It should be noted that y-coordinates of signals can be sorted either in an ascending or a descending order and the method of separating rows of signals can work in a similar way. The micro-wells in a dPCR chip are arranged in regular horizontal rows and vertical columns. For an un-tilted dPCR chip, differences of the y-coordinates of micro-wells within the same row are small compared to those between different rows. If y-coordinates of all the micro-wells are sorted in an ascending order, y-coordinates of the same row will be clustered together and there will be a sudden big change, called a break point, between a y-coordinate cluster of one row and a y-coordinate cluster of the next row. Each cluster of micro-wells with close y-coordinates is assigned to one row. The break point can be used as a marker to separate one row from another. The break points can be found, for example, by sorting raw y-coordinates of all the micro-wells in an ascending order in an Excel spreadsheet. Starting from the first micro-well with the smallest y-coordinate, micro-wells belonging to the first row can be identified. If there are n micro-wells on the first row, the difference of y-coordinate value between the $n^{th}$ and $(n+1)^{th}$ micro-well will be significantly higher than those among the n micro-wells of the first row. The $(n+1)^{th}$ micro-well is considered to be a micro-well of the second row. The sudden increase of change in y-coordinate value between the $n^{th}$ and $(n+1)^{th}$ micro-well is considered a "break point" that separates the first row from the second row. The other rows can be sequentially identified using the same method. The break points can also be found by plotting y-coordinates of all the micro-wells in an ascending order. Micro-wells of the same row will be clustered together. A sudden jump, that is a break point, in y-coordinate value can be identified that separates clusters of micro-wells of different rows. By searching for break points in the sorted y-coordinates, different rows of micro-wells containing fluorescence signals can be identified. The identified rows are assigned with preliminary row numbers ordered by the ascending y-coordinate values. For example, the row with the lowest y-coordinate is the assigned as the first row. The row with the second lowest y-coordinate is assigned as the second row, etc.

There are several criteria to determine whether the rows are correctly identified. First, the total number of identified rows should not be larger than 2 folds of the known number of rows on a dPCR chip. Theoretically, the number of identified rows should be known number of rows built on the dPCR chip. In practice, the number of identified rows can be larger than the theoretical number. For example, for a dPCR chip of 200 rows, the maximum number of identified rows should not be larger than 250, 300 or 350. If the number of rows identified by this method is more than 2 folds of the known number of rows built on the dPCR chip, it is an indication that the y-coordinate break point method fails. It is also an indication that the dPCR image is tilted and y-coordinate needs to be adjusted. Second, the maximum number of micro-wells in identified rows should not be larger than 2 folds of the known number of columns on a dPCR chip. Theoretically, the number of micro-wells in a row should be the known number of columns built on the dPCR chip. In practice, the number of micro-wells in an identified row can be larger than the theoretical number. For example, for a dPCR chip of 150 columns, the maximum number of micro-wells in an identified row should not be larger than 200, 250 or 280. If the number of micro-wells in a row identified by this method is more than 2 folds of the known number of columns built on the dPCR chip, it is an indication that the y-coordinate break point method fails. It is also an indication that the dPCR image is tilted and y-coordinate needs to be adjusted. Third, the number of short rows should be less than half of the total number of rows. Short rows are rows having significantly less micro-wells than the known number of columns in a dPCR chip. Short rows are usually located at the edge of a dPCR chip. For example, a short row may have less than 6, 8 or 10 micro-wells. Only when all of the three requirements above are satisfied, it is considered that the rows are successfully separated using the y-coordinate break point method. In a good separation, break points are clearly distinguishable and the number of micro-wells is close to the known number of columns in a dPCR chip. This is an indication that the image of the dPCR chip is not tilted and can be used for alignment with a chip grid without adjustment of raw coordinates.

Under some circumstances, break points for separating different rows are not distinguishable in the raw data of y-coordinates obtained directly from image processing. This could happen when a dPCR chip image is tilted and rows of micro-wells are not horizontal in regard to the X-axis. As a result, a y-coordinate of a lower number row can be larger than that of a higher number row, which will mix the y-coordinates in different rows and disrupt break points in the sorted y-coordinates. Plotting the sorted y-coordinates in an ascending order will generate a continuously ascending line without distinguishable break points (see FIG. 2). If this is the case, the y-coordinates need to be adjusted until break points can be clearly distinguished and rows of micro-wells can be successfully identified according to the criteria outlined above.

In some embodiments of the invention, a method is provided to adjust y-coordinates of signals of micro-wells of a dPCR chip so that break points for separating rows of micro-wells can be clearly identified. The raw y-coordinate is adjusted as following:

$$y'=y+k*x$$

wherein y' is an adjusted y-coordinate, y is a raw y-coordinate, x is a raw x-coordinate, k is a correction factor that can be changed in value.

Figure 2:
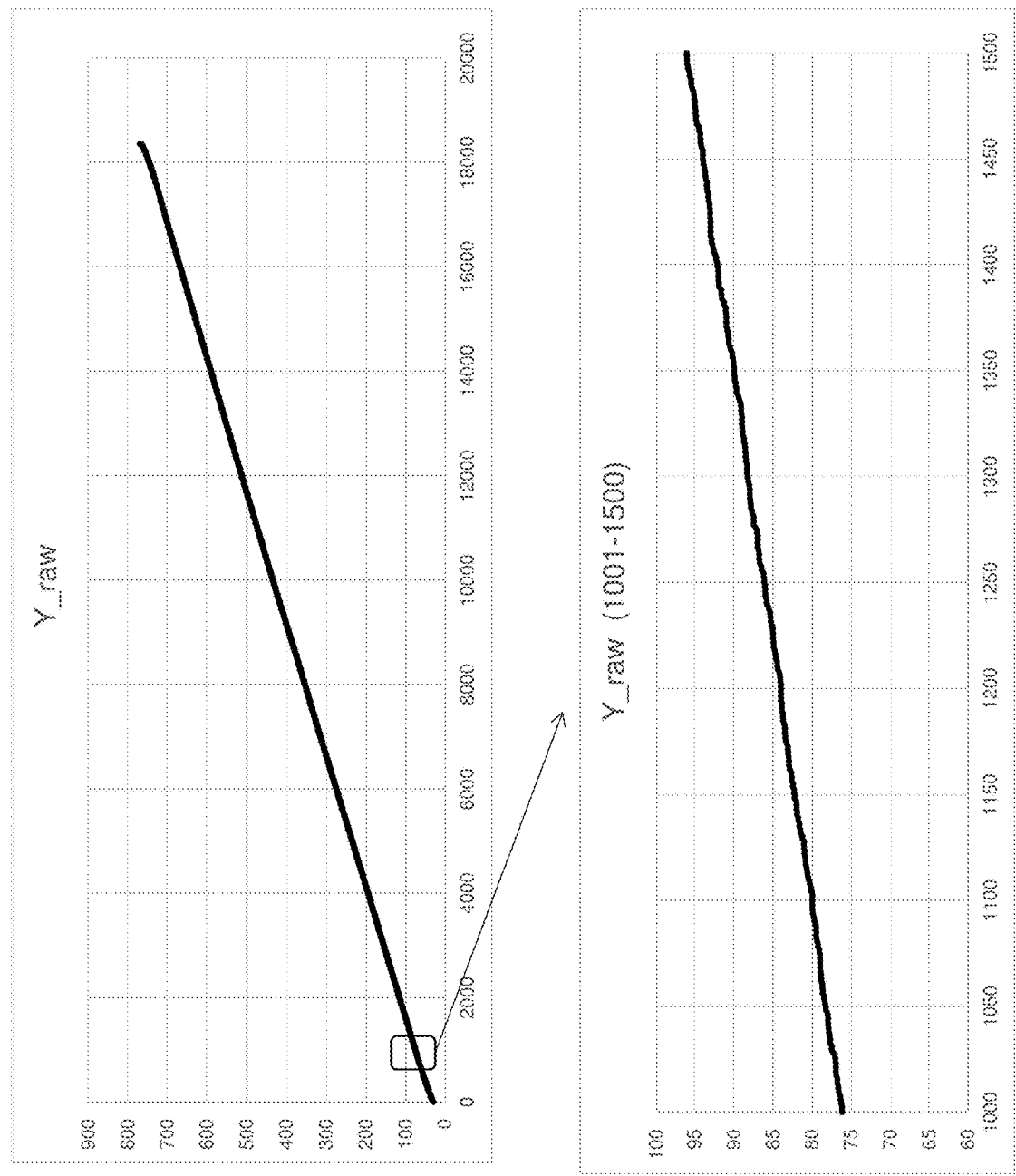
FIG. 2 is a plot of sorting in an ascending order of raw y-coordinates of all signals of micro-wells on a dPCR chip.
Figure 3:
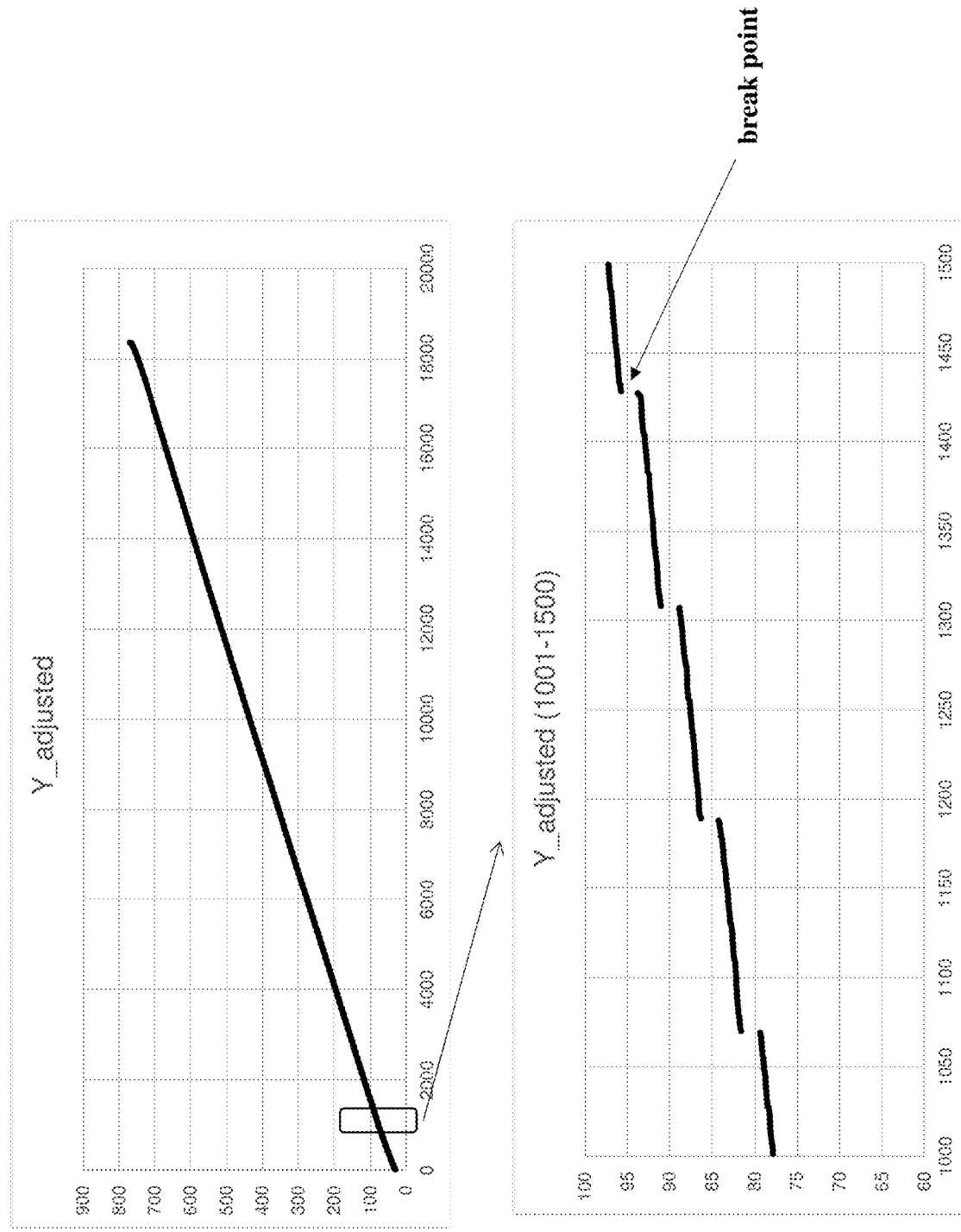
FIG. 3 is a plot of sorting in an ascending order of adjusted y-coordinates of all signals of micro-wells on the same dPCR chip as that of FIG. 2.

The correction factor k is changed to find an appropriate $k_c$ where break points can be clearly distinguished in sorted y'-coordinates ($y'=y+k_c*x$). FIG. 2 shows a plot of sorting raw y-coordinates and FIG. 3 shows a plot of sorting y'-coordinates adjusted by an appropriate correction factor $k_c$. In the zoom-in plot of FIG. 2, it can be seen that the sorted raw y-coordinates shows a continuous line without any discernable break points. In the zoom-in plot of FIG. 3, it can be seen that the sorted y'-coordinates shows clustered rows of micro-wells separated by clear break points. When break points can be found in the sorted y'-coordinates, the break points can be used to separate rows of micro-wells in a dPCR chip as described above. The correction factor k is related to the tilting angle of the dPCR chip. The expected k values can range from, for example, −0.5 to 0.5, −1 to 1, or −5 to +5. The appropriate $k_c$ is not a unique value. Any correction factor k is sufficient if, after converting raw y-coordinates to adjusted y'-coordinate, break points can be clearly distinguished in adjusted y'-coordinates sorted in an ascending order. A set of adjusted y'-coordinates (y'=y+$k_c$*x) are thus obtained.

After the y-coordinates are adjusted, the x-coordinates also need to be adjusted. In some embodiment of the invention, it provides a x-coordinate break point method for separating columns of signals in an image by finding a break point in x-coordinates of signals sorted in an ascending order. The micro-wells in a dPCR chip are arranged in regular horizontal rows and vertical columns. For an untilted dPCR chip, differences of the x-coordinates of micro-wells within the same column are small compared to those between different columns. If x-coordinates of all the micro-wells are sorted in an ascending order, x-coordinates of the same column will be clustered together and there will be a break point between a x-coordinate cluster of one column and a x-coordinate cluster of the next column. Each cluster of micro-wells with close x-coordinates is assigned to one column. The break point can be used as a marker to separate one column from another. By searching for break points in the sorted x-coordinates, different columns of micro-wells containing fluorescence signals can be identified. The identified columns are assigned with preliminary column numbers ordered by the ascending x-coordinate values. For example, the column with the lowest x-coordinate is the assigned as the first column. The column with the second lowest x-coordinate is assigned as the second column, etc.

There are several criteria to determine whether the columns are correctly identified. First, the total number of identified columns should not be larger than 2 folds of the known number of columns on a dPCR chip. Theoretically, the number of identified columns should be the known number of columns in a dPCR chip. In practice, the number of identified columns can be more than the theoretical number. For example, for a dPCR chip of 150 columns, the maximum number of identified columns should not be larger than 180, 200 or 250. The maximum number of identified columns is empirically determined. Second, the maximum number of micro-wells in identified columns should not be larger than 2 folds of the known number of rows on a dPCR chip. For example, for a dPCR chip of 200 rows, the maximum number of micro-wells in an identified column should not be larger than 220, 300 or 350. Third, the number of short columns should be less than half of the total number of columns. Short columns are columns having significantly less micro-wells than the known number of rows in a dPCR chip. Short columns are usually located at the edge of a dPCR chip. For example, a short column may have less than 6, 8 or 10 micro-wells. Only when all of the three requirements are satisfied, it is considered that the columns are successfully separated using the x-coordinate break point method. If this is the case, the raw x-coordinates can be directly used for alignment to a chip grid without adjustment.

Under some circumstances, break points for separating different columns are not distinguishable in the raw data of x-coordinates obtained directly from image processing. This could happen when a dPCR chip image is tilted and columns of micro-wells are not vertical in regard to the x-axis. As a result, a x-coordinate of a lower number column can be larger than that of a higher number column, which will mix the x-coordinates in different columns and disrupt break points in the sorted x-coordinates. Plotting the sorted x-coordinates in an ascending order will generate a continuously ascending line without distinguishable break points. If this is the case, the x-coordinates need to be adjusted until break points can be clearly distinguished and columns of micro-wells can be successfully identified according to the criteria outlined above.

In some embodiments of the invention, a method is provided to adjust x-coordinates of signals of micro-wells of a dPCR chip so that break points for separating columns of micro-wells can be distinguished. The raw x-coordinate is adjusted as following:

$$x'=x+k*y$$

wherein x' is adjusted x-coordinate, y is raw y-coordinate, x is raw x-coordinate, k is a correction factor that can be changed in value.

The correction factor k is changed to find an appropriate $k_c$ (x'=x+$k_c$*y) where break points can be clearly distinguished in sorted x'-coordinates. When break points can be found in the x'-coordinates, the break points can be used to separate columns of micro-wells in a dPCR chip as described above. The expected k values may range from, for example, −0.5 to 0.5, −1 to 1, or −5 to +5. The appropriate k is not a unique value. Any correction factor k is sufficient if, after converting raw x-coordinates to adjusted x'-coordinate, break points can be clearly distinguished in adjusted x'-coordinates sorted in an ascending order. A set of adjusted x'-coordinates (x'=x+$k_c$*y) is thus obtained.

Figure 4:
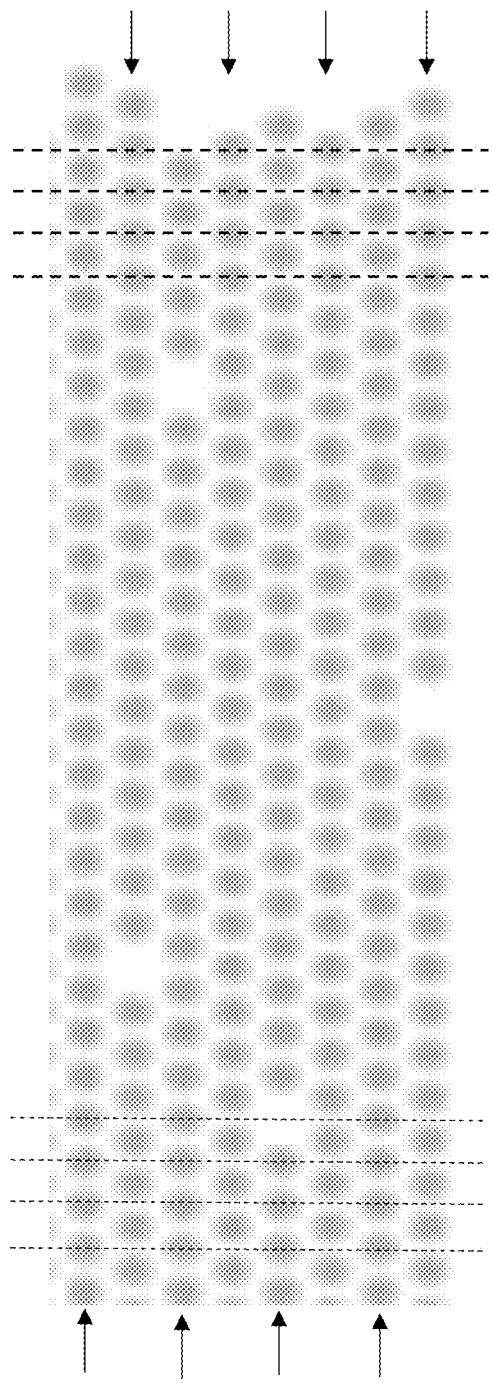
FIG. 4 shows an image of fluorescence signals of micro-wells on a dPCR chip.

In some embodiments, x-coordinates from selected rows of micro-well signals are sorted and used for separating columns. This selection method can be advantageous under certain configurations. For example, columns may be alternatively intersected with odd or even rows only as shown in FIG. 4. In this configuration, the columns intersected with old rows and even rows can be analyzed separately. If the distance between to two adjacent columns is bigger, it is easier to find break points to separate two columns and it is less likely to make mistakes in separating different columns. In some embodiments, x-coordinates for odd rows are selected and sorted in an ascending order. Columns having intersection with odd rows are identified using the x-coordinate break point method described above. X-coordinates for even rows are then selected and sorted in an ascending order. Columns having intersection with even rows are identified using the x-coordinate break point method described above. Combining columns intersecting with odd rows and columns intersecting with even rows, columns for all the micro-wells can be determined.

Figure 5:
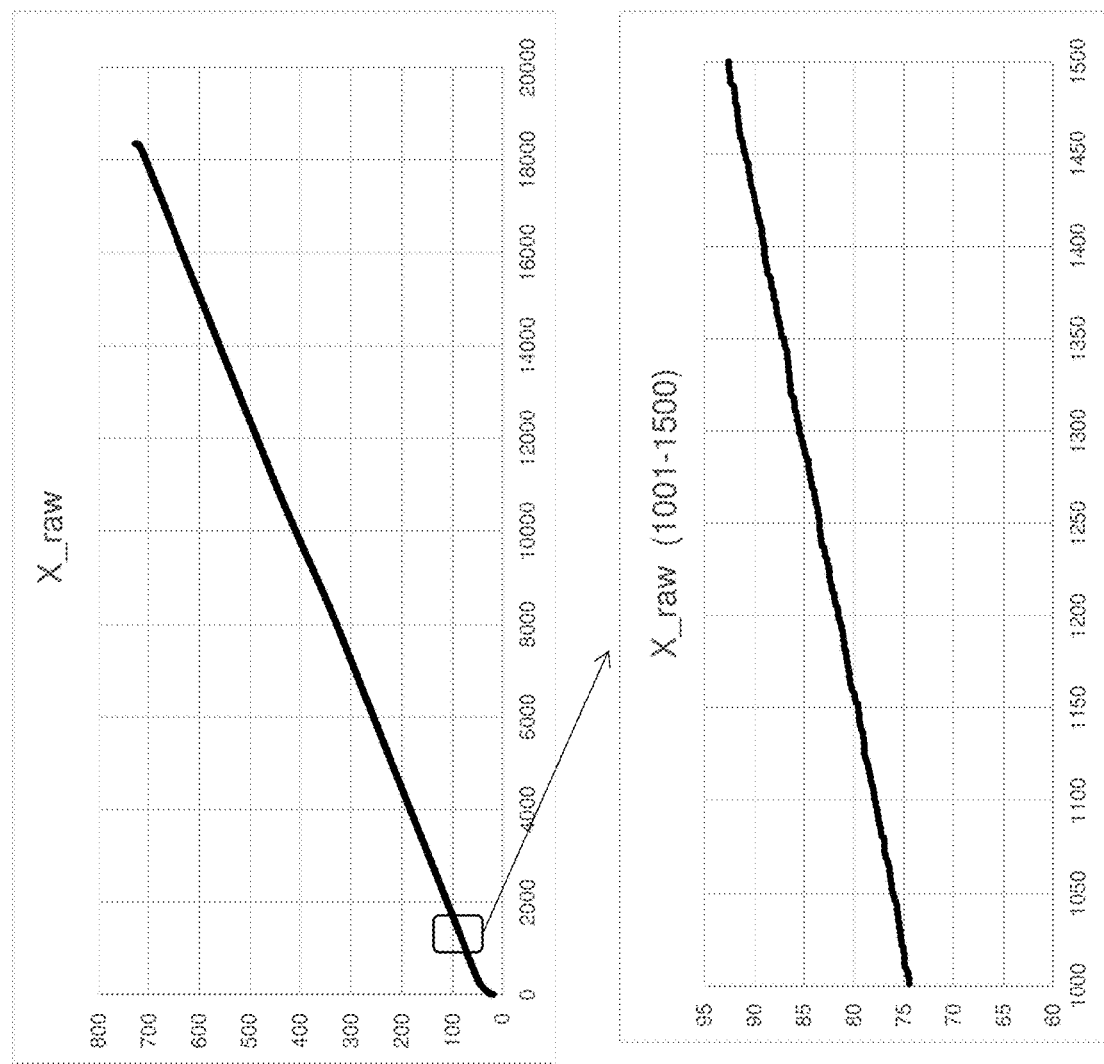
FIG. 5 is a plot of sorting in an ascending order of raw x-coordinates of all signals of micro-wells on a dPCR chip.
Figure 6:
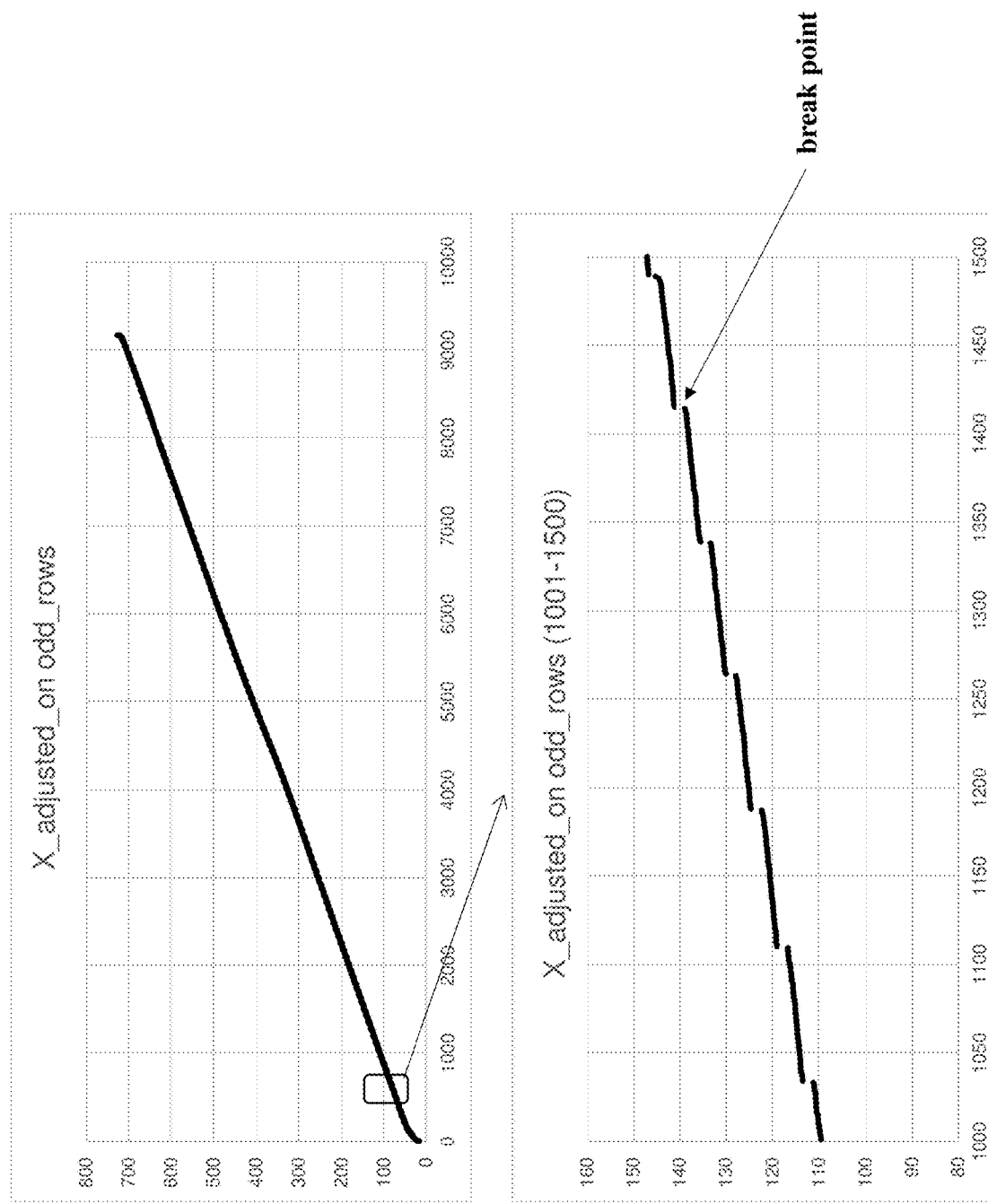
FIG. 6 is a plot of sorting in an ascending order of adjusted x-coordinates of signals of odd rows of micro-wells on the same dPCR chip as that of FIG. 5.

FIG. 5 shows a plot of sorting raw x-coordinates of all micro-wells and FIG. 6 shows a plot of sorting x'-coordinates of micro-wells on odd rows adjusted by an appropriate $k_c$. In the zoom-in plot of FIG. 5, it can be seen that the sorted x-coordinates shows a continuous line without any discernable break points. In the zoom-in plot of FIG. 6, it can be seen that the sorted x'-coordinates shows clustered columns of micro-wells separated by clear break points.

After adjusting the y- and x-coordinates of the signals, a set of adjusted coordinates (x', y') are obtained for all the signals of micro-wells in the dPCR chip, which produces an adjusted image that can be used to align to a chip grid. The chip grid is a manufacture layout for arranging micro-wells on a dPCR chip. Each dPCR chip has a fiducial marker placed at a preset location of the chip, which appears in the image produced and can be used as a point of reference for alignment. The adjusted image is aligned to the chip grid by aligning the position and the shape of the fiducial marker in both the image and the chip grid. This is achieved by creating a filter with the shape of the fiducial marker and running the filter across the adjusted image to find the position of the fiducial marker. When the filter is aligned with the fiducial marker in the adjusted image, the distance error between the filter and the image will be at a minimum value. The location of the minimum error value is considered the location of the fiducial marker. The adjusted image and the chip grid can be aligned by overlaying of the fiducial marker. Once aligned, the coordinates of micro-wells in the image can be converted to the corresponding grid coordinates defining the row and column position for each micro-well. Since the chip layout is known, it can also be used to remove any points which do not match up with the layout.

In one embodiment of the invention, there provides a method for aligning an image of signal spots of micro-wells of a dPCR chip to a grid, comprising the steps of: 1) obtaining position coordinate (x,y) for each signal spots of micro-wells of the dPCR chip; 2) selecting a number of random signal spots and calculating a root mean square distance between each selected signal spot and its nearest grid spot; 3) adjusting coordinates of the selected signal spots to find a best fit adjustment that the average root mean square distance for the selected random signal spots is at a minimum value; 4) performing the best fit adjustment to all the signal spots to obtain adjusted coordinates for all the signal spots; and 5) aligning adjusted coordinates of signal spots of micro-wells of the dPCR chip to the grid by aligning to a fiducial marker in the dPCR chip.

The grid layout for a dPCR chip is known and the grid coordinate for each micro-well is known. In order to align all the signal spots on an image to the grid layout, a small number of random signal spots are selected to align to the grid first. This could significantly decrease the computation complexity. The number of selected random signal spots can be at least 10, 20, 30, 40, 50, 60, 70, 80, 90, 100, 200, 500 or 1000.

Root mean square (RMS) distance is a measure of the mismatch between signal spots to the nearest grid spots. If all the signal spots are perfectly matched to the grid spots, the RMS distance is 0. RMS distance is calculated as the following:

$$\text{RMS distance} = \frac{\sum_{i=1}^{T} \sqrt{(x_{1,i} - x_{2,i})^2 + (y_{1,i} - y_{2,i})^2}}{T}$$

wherein $X_{1,i}$ is the x-coordinate of $i^{th}$ signal spot, $y_{1,i}$ is the y-coordinate of $i^{th}$ signal spot, $x_{2,i}$ is the x-coordinate of the grid spot nearest to the $i^{th}$ signal spot, $y_{2,i}$ is the y-coordinate of the grid spot nearest to the $i^{th}$ signal spot, and T is the number of selected signal spots. The alignment is to find a position that the RMS distance is at a minimum value. To align the selected signal spots to the grid, the coordinates of these signal spots are adjusted multiple times to find the position with the minimum RMS distance.

In some embodiments, the selected signal spots are rotated and their coordinates are adjusted as following: x'=x+k*y, y'=y−k*x, wherein x' is an adjusted x coordinate, y is an adjusted y coordinate, x is a raw x coordinate, y is a raw y coordinate, and k is a correction factor that can be varied. In some embodiments, the selected signal spots are translated and their coordinates are adjusted as following: x'=x+a, y'=y+b, wherein x' is an adjusted x coordinate, y is an adjusted y coordinate, x is a raw x coordinate, y is a raw y coordinate, a is a correction factor that can be varied, and b is a correction factor that can be varied. The correction factors a and b do not need to be the same.

After numerous adjustments with rotations and translations, the adjustment that produces a minimum RMS distance, called the best fit adjustment, can be found. This best fit adjustment can then be applied to all the signal spots to make an adjusted image. This adjusted image can be used to align to the grid spots using the built-in fiducial marker as described above.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for aligning an image of signals of micro-wells of a dPCR chip to a grid, comprising the steps of:
   1) obtaining position coordinate (x,y) for each signal of micro-wells of the dPCR chip;
   2) adjusting y-coordinates of signals of micro-wells of the dPCR chip using a y-coordinate break point method to obtain adjusted y'-coordinates for signals and identify rows of signals of micro-wells in the dPCR chip;
   3) adjusting x-coordinates of signals of micro-wells of the dPCR chip using a x-coordinate break point method to obtain adjusted x'-coordinates for signals of micro-wells of the dPCR chip; and
   4) aligning adjusted coordinates (x', y') of signals of micro-wells of the dPCR chip to a grid by aligning to a fiducial marker in the dPCR chip.

2. The method of claim 1, wherein the y-coordinate break point method comprises the steps of:
   a. sorting y-coordinates of all the signals of micro-wells of the dPCR chip in an ascending order;
   b. keeping adjusted y'=y, if it is possible to use break points in sorted y'-coordinates to separate one row of signals from an adjacent row of signals;
   c. if it is not possible to directly use break points to separate one row of signals from an adjacent row of signals, adjusting y-coordinate of each signal as following:
      y'=y+k*x, wherein y' is an adjusted y-coordinate, y is a raw y-coordinate, x is a raw x-coordinate, and k is a correction factor that can be changed;
   d. sorting y'-coordinates of all the signals in an ascending order;
   e. finding an appropriate $k_c$ such that it is possible to use break points to separate one row of signals from an adjacent row of signals in sorted y'; and
   f. obtaining adjusted y'-coordinates for signals of micro-wells in the dPCR chip, wherein y'=y+$k_c$*x.

3. The method of claim 1, wherein the x-coordinate break point method comprises the steps of:
  a. sorting x-coordinates of signals of selected rows of micro-wells of the dPCR chip in an ascending order;
  b. keeping adjusted x'=x, if it is possible to use break points in sorted y'-coordinates to separate one column of signals from an adjacent column of signals;
  c. if it is not possible to directly use break points to separate one column of signals from an adjacent column of signals, adjusting y-coordinate of each signal as following:
    x'=x+k*y, wherein x' is adjusted x-coordinate, y is raw y-coordinate, x is raw x-coordinate, and k is a correction factor that can be changed;
  d. sorting x'-coordinates of signals in an ascending order;
  e. finding an appropriate $k_c$ such that it is possible to use break points to separate one column of signals from an adjacent column of signals in sorted x'-coordinates;
  f. obtaining adjusted x'-coordinates for signals of micro-wells in the dPCR chip, wherein x'=x+$k_c$*y.

4. The method of claim 3, wherein selected rows of signals are all the identified rows of signals.

5. The method of claim 3, wherein selected rows of signals are odd number or even number rows of signals, wherein the x-coordinate break point method is used separately on signals of odd number or even number rows to obtain adjusted x'-coordinates for all the signals of micro-wells in the dPCR chip.

6. A method for aligning an image of signal spots of micro-wells of a dPCR chip to a grid, comprising the steps of:
  1) obtaining position coordinate (x,y) for each signal spots of micro-wells of the dPCR chip;
  2) selecting a number of random signal spots and calculating a root mean square distance between selected signal spots and nearest grid spots;
  3) adjusting coordinates of the selected signal spots to find a best fit adjustment that the root mean square distance for the selected random signal spots is at a minimum value;
  4) performing the best fit adjustment to all the signal spots to obtain adjusted coordinates for all the signal spots; and
  5) aligning adjusted coordinates of signal spots of micro-wells of the dPCR chip to the grid by aligning to a fiducial marker in the dPCR chip.

7. The method of claim 6, wherein the coordinates of the selected signal spots is adjusted as following: x'=x+k*y, y'=y−k*x, wherein x' is an adjusted x coordinate, y is an adjusted y coordinate, x is a raw x coordinate, y is a raw y coordinate, and k is a correction factor that can be varied.

8. The method of claim 6, wherein the coordinates of the selected signal spots is adjusted as following: x'=x+a, y'=y+b, wherein x' is an adjusted x coordinate, y is an adjusted y coordinate, x is a raw x coordinate, y is a raw y coordinate, a is a correction factor that can be varied, and b is a correction factor that can be varied.

9. The method of claim 6, wherein the number of selected random signal spots is at least 10, 20, 30, 40, 50, 60, 70, 80, 90, 100, 200, 500 and 1000.

* * * * *